United States Patent [19]
Kruse

[11] 3,935,284
[45] Jan. 27, 1976

[54] HOMOGENEOUS HYDROGENATION OF SACCHARIDES USING RUTHENIUM TRIPHENYL PHOSPHINE COMPLEX

[75] Inventor: Walter M. Kruse, Wilmington, Del.

[73] Assignee: ICI United States Inc., Wilmington, Del.

[22] Filed: Oct. 19, 1973

[21] Appl. No.: 407,871

[52] U.S. Cl. ...... 260/635 C; 252/431 P; 260/488 J; 260/633; 260/635 A
[51] Int. Cl.² ......................................... C07C 29/00
[58] Field of Search ............. 260/635 C; 252/431 P

[56] References Cited
UNITED STATES PATENTS

| | | | |
|---|---|---|---|
| 2,209,055 | 7/1940 | Hanford | 260/635 C |
| 2,325,206 | 7/1943 | Stengel | 260/635 C |
| 2,518,235 | 8/1950 | Hartstra et al. | 260/635 C |
| 2,759,023 | 8/1956 | Kool et al. | 260/635 C |
| 2,868,847 | 1/1959 | Boyers | 260/635 C |
| 2,892,801 | 6/1959 | Sargent | 260/635 C |
| 3,454,644 | 7/1969 | Dewhirst | 260/638 B |
| 3,488,400 | 1/1970 | Candlin et al. | 260/677 |
| 3,767,709 | 10/1973 | Fenton | 252/431 P |
| 3,793,355 | 2/1974 | Wilkinson et al. | 252/431 P |
| 3,804,868 | 4/1974 | Chabardes et al. | 252/431 P |
| 3,804,869 | 4/1974 | Chabardes et al. | 252/431 P |

Primary Examiner—Joseph E. Evans

[57] ABSTRACT

A homogeneous hydrogenation process is disclosed. The process, which is useful in the preparation of hydrogenated derivatives of compounds selected from the group consisting of monosaccharides, disaccharides, trisaccharides, polysaccharides, corn starch hydrolyzate, and compounds represented by the formula $RH_2C—CO—CH_2R$ wherein R is hydroxyl or halogen, comprises contacting a solution of one of these compounds with hydrogen in the presence of a catalyst comprising a ruthenium triphenyl phosphine complex and a strong acid.

17 Claims, No Drawings

1

HOMOGENEOUS HYDROGENATION OF SACCHARIDES USING RUTHENIUM TRIPHENYL PHOSPHINE COMPLEX

BACKGROUND OF THE INVENTION

1. Field of the Invention

The present invention relates generally to a homogeneous hydrogenation process. More particularly, the invention relates to a homogeneous hydrogenation process comprising contacting a solution of a compound selected from the group consisting of monosaccharides, disaccharides, trisaccharides, polysaccharides, corn starch hydrolyzate, and compounds having the formula $RH_2C-CO-CH_2R$ wherein R is hydroxyl or halogen with hydrogen in the presence of a catalyst comprising a ruthenium triphenyl phosphine complex and a strong acid.

2. Description of the Prior Art

The hydrogenation of a variety of organic compounds by contacting a solution of the compound with molecular hydrogen in the presence of a hydrogenation catalyst is well-known in the art. As is also well-known, hydrogenation processes are generally classifiable into one of two broad catagories, depending upon the physical phase in which the catalyst is present during the hydrogenation process. In the first type, referred to as a heterogeneous hydrogenation process, the catalyst is essentially insoluble in the reaction medium. By comparison, in the second type, referred to as a homogeneous hydrogenation process, the catalyst is essentially completely soluble in the reaction medium.

The use of ruthenium-containing materials as catalysts in both heterogeneous and homogeneous hydrogenation processes has also been reported. In U.S. Pat. No. 2,868,847 issued to Boyers, it is disclosed that ruthenium-containing catalysts may be utilized in a heterogeneous process for preparing hydrogenated derivatives of mono- and di-saccharides. In U.S. Pat. No. 3,454,644 issued to Dewhirst, a homogeneous hydrogenation process is disclosed utilizing a ruthenium or osmium metal complex as a catalyst and a high hydrogen pressure. Among the various ligands described as useful in said complexes are several tertiary phosphines, including triphenyl phosphine.

It is an object of the present invention to provide a homogeneous process for the preparation of hydrogenated derivatives of certain compounds containing an activated carbonyl group.

SUMMARY OF THE INVENTION

In accordance with the present invention, it has been found that hydrogenated derivatives of compounds selected from the group consisting of monosaccharides, disaccharides, trisaccharides, polysaccharides, corn starch hydrolyzate, and compounds represented by the formula $RH_2C-CO-CH_2R$ wherein R is hydroxyl or halogen, can be prepared in a homogeneous process by contacting a solution of the compound with hydrogen in the presence of a catalyst comprising a ruthenium triphenyl phosphine complex and a strong acid.

DESCRIPTION OF THE PREFERRED EMBODIMENTS

As mentioned above, in accordance with the present invention it has been discovered that certain compounds containing an activatable carbonyl group may be converted to their hydrogenated derivatives in a homogeneous process if the reaction is carried out in the presence of a specific ruthenium catalyst. In this regard it should be noted that the key to the present invention is the selection of a particular catalyst for the substrate being hydrogenated. Thus, it has been found that for substrates selected from the above-mentioned group, it is essential that the catalyst employed be a ruthenium triphenyl phosphine complex. As was also mentioned above, it has also been found in accordance with the present invention that improved results are achieved if the catalyst contains, in addition to the ruthenium triphenyl phosphine, a strong acid. The substrates, catalysts, solvents, and reaction conditions which may be employed in carrying out the present invention are described in detail below.

Substrate

As was mentioned above, the substrates which may be hydrogenated in accordance with the present invention are selected from the group consisting of monosaccharides, disaccharides, trisaccharides, polysaccharides, corn starch hydrolyzate, and compounds having the formula $RH_2C-CO-Ch_2R$ wherein R is hydroxyl or halogen.

The monosaccharides which may be hydrogenated in the homogeneous process of the present invention are those containing at least 4 carbon atoms. Preferred results are achieved with monosaccharides containing from 4 to 6 carbon atoms. As used herein, the term monosaccharides includes both aldoses and ketoses. Representative aldoses — i.e., monosaccharides containing a terminal aldehyde (—CHO) group — which may be employed include, for example, glucose, arabinose, and glactose. Representative ketoses — i.e., monosaccharides containing a keto (>C=O) group — which may be employed include, for example, fructose and ribulose.

The di- tri- and poly-saccharides which may be hydrogenated by the process of the present invention are compounds containing, respectively, two, three and more than three of the above-mentioned monosaccharide units. Representative disaccharides which may be employed include, for example, sucrose, maltose and lactose. Representative trisaccharides include raffinose and the polysaccharides include, for example, starch, dextrin, glycogen, and inulin.

An additional substrate which may be hydrogenated in accordance with the improved process of the present invention is referred to as corn starch hydrolyzate. As used herein, this term refers to a material prepared by hydrolyzing corn starch with a combination of an acid and an enzyme and removing from the resulting product most of the glucose produced thereby. The remaining corn starch hydrolyzate generally contains from about 60 percent to about 65 percent dextrose; from about 15 percent to about 20 percent disaccharide; and from about 15 percent to about 25 percent trisaccharides and polysaccharides.

Substrates having the following formula may also be hydrogenated in the homogeneous process of the present invention:

$$RH_2C-CO-CH_2R$$

wherein R is hydroxyl or halogen. Representative compounds having the above-mentioned formula include, for example, 1,3-dihydroxy acetone and 1,3-dichloro acetone.

Of these substrates the process of the present invention has been found to be particularly useful in hydrogenating monosaccharides.

Catalyst

As was also mentioned above, the catalyst employed in the process of the present invention comprises
a. a ruthenium triphenyl phosphine, and
b. a strong acid.

The active form of the ruthenium triphenyl phosphine compounds which may be utilized in accordance with the present invention is represented by the following formula:

$$RuHCl(Pr'_3)_3$$

wherein R' is phenyl or a substituted phenyl selected from the group consisting of para-methyl phenyl and para-methoxy phenyl. In accordance with the present invention it has been found that ligands other than those mentioned above, including other tertiary phosphines, do not produce satisfactory results when employed in a homogeneous process for hydrogenating the substrates employed herein.

The active form of the ruthenium triphenyl phosphine may be introduced into the hydrogenation reaction mixture by any one of the following three methods.

First, the active form may be prepared, isolated, and introduced directly into the reaction medium. If this procedure is utilized the material is prepared in a two step process in accordance with the following reactions:

(a) $2RuCl_3 \cdot 3H_2O + 3PR_3 \rightarrow 2RuCl_2(PR_3)_3 +$ $$\overset{O}{\underset{\|}{P}}R_3 + 2HCl + 2H_2O$$

b. $RuCl_2(PR_3)_3 + H_2 \rightarrow RuHCl(PR_3)_3 + HCl$

Reaction (a) may be carried out by the procedure described in Stephenson et al., *J. Inorg. Nuclear Chem.*, 1966, Vol. 28 page 945. Reaction (b) may be carried out by the procedure described in Hallman et al., *J. Chem. Soc.* (A), 1968, page 1343.

Alternately, the active form may be prepared in situ in the reaction medium either by adding the dichloro derivative, prepared as in reaction (a) above, to the reaction mixture or by adding the starting materials as employed in reaction (a) above to said mixture. Preferred results are achieved when the starting materials — i.e., the ruthenium chloride and the triphenyl phosphine — are added to the reaction mixture and the active catalyst is formed in situ. When this procedure is employed, it has been found that the molar ratio of triphenyl phosphine to ruthenium chloride is preferably equal to at least 2 to 1. At ratios below this amount, the rate of the hydrogenation reaction is considerably slower and, although the reaction rate does increase somewhat as this ratio is increased, the further increase does not justify the larger amounts of triphenyl phosphine required.

In addition to the specific ruthenium triphenyl phosphine described above, the catalysts useful in the process of the present invention also include a strong acid. It has been found that the inclusion of a small amount of such an acid results in an unexpected increase in the rate of the hydrogenation reaction. As used herein, the term strong acid refers to acids which have a $pK_a$ value equal to less than about 1.

Representative acids which may be employed in the catalyst useful in the present invention include, for example, hydrochloric acid; sulfuric acid; sulfonic acids such as toluene sulfonic acids; trifluoromethyl sulfonic acid ($CF_3SO_3H$) and fluoboric acid ($HBF_4$). Of these it is preferred to employ hydrochloric acid. In this regard it should be noted that when the ruthenium triphenyl phosphine component of the catalyst is prepared in situ by either of the previously described methods 1 mol of hydrochloric acid is generated for each mol of the triphenyl phosphine prepared. Thus it is possible to prepare in situ both components of the catalyst system utilized herein.

Process

In carrying out the present invention the substrate is dissolved in a suitable solvent and the catalyst is added thereto. Hydrogen is then introduced into the reaction mixture until the substrate has been hydrogenated to the extent desired.

Any solvent which is chemically inert and which does not interfere with the hydrogenation reaction may be employed. However, it is emphasized that the particular solvent employed must be one in which both the substrate and the catalyst are soluble either at room temperature or at the temperature at which the reaction is carried out. A preferred class of solvents which may be utilized are those referred to as organic, polar solvents. As used herein, the term polar solvents includes those which have a dielectric constant equal to at least about 20. Representative solvents which may be utilized include, for example, methanol, ethanol, methyl cellosolve and acetic acid. The amount of solvent employed has not been found to be narrowly critical to the present invention and any amount of solvent which will dissolve the substrate and catalyst may be employed. However, it is critical that the solvent be prototropic — i.e., have an active hydrogen available.

In carrying out the present invention there should also be included as part of the solvent system an amount of water equal to from about 1 percent to about 30 percent by weight based on the total weight of said system. As is apparent from Examples 19 and 20, the water need not be added as much.

A further improvement in the process of the present invention has been achieved by including a weakly basic solvent in the system and, while it is not essential to the present invention, there is preferably included in the reaction mixture an amount of such a solvent. The advantage of including such a material in the reaction mixture is to increase the solubility of the ruthenium triphenyl phosphine. As used herein, the term weakly basic solvent refers to materials having a $K_b$ value equal to less than about $1 \times 10^{-13}$ — i.e., a $pK_b$ equal to less than about 13. Representative weakly basic solvents which may be employed include, for example, dimethylformamide, N-methylpyrrolidone, and diethylacetamide. When a weakly basic solvent is utilized it should be employed in an amount equal to at least one mol for each mol of strong acid in the reaction mixture.

An especially preferred solvent system for use in carrying out the present invention comprises N-methylpyrrolidone, methyl cellosolve and water in a ratio, by volume, of 15:15:2.

The substrate concentration has not been found to be critical to the process of the present invention. However, as this concentration decreases the rate of the reaction generally increases.

Concerning the catalyst concentration, this also has not been found to be narrowly critical to the process of the present invention. Thus, any amount of catalyst which is both soluble in the reaction mixture and which is sufficient to accelerate the reaction may be employed. Preferred results have been achieved with catalyst concentrations equal to from about 0.25 gram to about 0.5 gram per 40 grams of substrate being hydrogenated.

The hydrogenation process of the present invention is carried out utilizing techniques and apparatus which are wellknown to those skilled in the art except as otherwise noted herein.

The reaction temperature employed in the hydrogenation process may be varied over a wide range. However, preferred results are achieved at temperatures in the range of from about 75°C. to about 150°C. It has been found that at temperatures below about 75°C. the rate of reaction is slow and, therefore, may not be practical. It should also be noted that, in some instances, depending upon the substrate being hydrogenated, the catalyst and the solvent employed, it may be necessary to employ heat to achieve a complete solution of the substrate and catalyst in the solvent. However, it has also been found that at temperatures above about 150°C. no further increase in the reaction rate is noted and it is, therefore, not preferred to carry out the reaction at temperatures much above 150°C. Also, at temperatures above about 150°C. the catalyst may not be stable and, due to decarbonylation of the substrate, carbonyl complexes of the ruthenium triphenyl phosphine may occur. These complexes are not efficient catalysts for the hydrogenation reaction.

Hydrogen is preferably introduced into the reaction mixture continuously during the course of the reaction and the reaction may be carried out under any positive hydrogen pressure. However, preferred results are achieved at hydrogen pressures of from about 20 to about 500 psi. Above about 500 psi, the reaction is pressure independent — i.e., there is no further increase in the reaction rate as the pressure is increased — and it is, therefore, not desirable to operate at a higher pressure. Also, at lower pressures the reaction times are longer than would be desirable in a commercial operation.

The reaction time depends upon the substrate, catalyst, pressure, and temperature employed. Generally, the reaction will be completed in reaction times of about 0.1 to about 3 hours.

The process of this invention may conveniently be carried out in any suitable type of apparatus which enables intimate contact with the reactants and control of the operating conditions. For example, the process of the present invention may suitably be carried out by passing, concurrently, the solutuion of substrate and catalyst upward through a vertical reactor and simultaneously passing a supply of hydrogen gas under pressure upward through the reactor. The process may be carried out in batch, semi-continuous or continuous operation and is preferably carried out in a continuous operation using a plurality of reactors arranged in a series.

In order to describe the present invention so that it may be more clearly understood, the following examples are set forth. These examples are set forth primarily for the purpose of illustration and any enumeration of detail contained therein should not be interpreted as a limitation on the concept of the present invention.

In the examples, low pressure hydrogenations — i.e., those at pressures up to about 60 psi hydrogen, were performed by the pop bottle technique described in Shriver, *Manipulation of Air Sensitive Compounds*, McGraw Hill, 1969, pages 156–158. Hydrogenations at higher pressures were carried out in a 300 ml stainless steel autoclave equipped with a temperature controller and temperature and pressure recorders. Samples were removed periodically during the course of the reaction, acetylated and analyzed by gas-liquid chromatography.

The half life period ($t_{1/2}$) refers to the time, in minutes, required for one half of the substrate to react to form the hydrogenated derivative thereof.

EXAMPLE 1

Preparation of ruthenium chloride triphenyl phosphine ($RuCl_2(P\phi_3)_3$).

Into a 200 ml pop bottle — i.e., a cappable, glass, pressure bottle, there was added a solution of 0.4 gram of ruthenium trichloride trihydrate dissolved in 50 ml of methanol and 2.4 grams of triphenyl phosphine. The bottle was evacuated and the reaction mixture stirred for 3 hours at 70°C. At the end of this time, the reaction mixture was cooled to room temperature, the brown crystals were removed by filtration and were washed with methanol. There resulted 1.5 grams of product identified as ruthenium chloride triphenyl phosphine. Analysis of the product indicated 9.3 percent phosphorus and 67.75 percent carbon. These compare favorably with the theoretical values of 9.7 percent phosphorus and 67.76 percent carbon.

EXAMPLE 2

Preparation of ruthenium hydridochloride triphenyl phosphine ($RuHCl(P\phi_3)_3$.

A solution was prepared comprising:
1.5 grams of ruthenium chloride triphenyl phosphine,
150 ml of degassed benzene, and
0.22 ml of triethylamine.

Hydrogen was bubbled through the solution for 15 hours at the end of which time the solution was filtered and the solvent evaporated until crystallization occurred. The crystals were filtered, washed with ether and dried.

EXAMPLE 3

Into a 200 ml pop bottle there we'e added:
40 grams of glucose,
0.5 grams of ruthenium chloride triphenyl phosphine prepared as described in Example 1, and
60 ml of ethanol.

The pop bottle was capped, evacuated to remove oxygen, and hydrogen introduced until a slight positive hydrogen pressure was achieved. The bottle was uncapped and the slurry transferred under a stream of nitrogen gas into a 300 ml stainless steel autoclave. The autoclave was closed, pressure tested, and hydrogen introduced to a pressure of 1,500 psi. At this point, heating was started and the reaction mixture was heated to a temperature of 110°C. During the heating period the pressure increased to 1,750 psi. Within 10 minutes the pressure dropped to 1,570 psi and no further change was noted. The reactor was cooled, the pressure released, and the autoclave opened at 50°C. The contents were transferred in a stream of nitrogen into a pop bottle and water was added to precipitate the catalyst. The catalyst was filtered from the aqueous reaction mixture and saved for use in a subsequent reaction. The water/ethanol mixture was removed in a vacuum oven. Analysis of the product indicated no residual glucose, and 90 percent by weight sorbitol.

EXAMPLE 4

Into a 200 ml pop bottle there were added:
10 grams of glucose,
10 ml of N-methyl-pyrrolidone,
15 ml of methyl cellosolve, and
2 ml of water.

The bottle was capped, evacuated to remove oxygen and a slight positive pressure of hydrogen introduces. The resulting solution was heated to 110°C and, to the solution there was added 0.25 grams of ruthenium chloride triphenyl phosphine prepared as described in Example 1, dissolved in 5 ml of N-methyl pyrrolidone. The hydrogen pressure was increased to 50 psi and the temperature of the reaction mixture maintained at 110°C. Samples of the reaction mixture were removed periodically during the course of the reaction and analyzed by gas-liquid chromatography. At the end of 30 minutes, ½ of the glucose had reacted — i.e., $t_{1/2}$ was equal to 30 minutes. At the end of 1 hour a sample contained 75 percent by weight sorbitol.

EXAMPLES 5 – 20

Employing the procedure described in Example 4, additional experiments were performed utilizing the substrate and catalyst concentrations, solvent systems and reaction conditions given in the following table. Results of the reactions are indicated, in most instances, by the time required for ½ of the substrate to be hydrogenated.

| Example | Glucose (grams) | RuCl$_2$(PO$_3$)$_3$ (grams) | Solvent* (ml) NMP | MC | H$_2$O | ETOH | HAL | Temp. °C. | Pressure psi | $t_{1/2}$ Minutes |
|---|---|---|---|---|---|---|---|---|---|---|
| 5 | 1 | 0.25 | 15 | 15 | 2 | | | 100 | 50 | 7.5 |
| 6 | 1 | 0.25 | 15 | 15 | 2 | | | 110 | 50 | 3.5 |
| 7 | 10 | 0.25 | 15 | 15 | 2 | | | 110 | 50 | 30 |
| 8 | 10 | 0.25 | 15 | 15 | 2 | | | 120 | 50 | 45 |
| 9 | 10 | 0.25 | 15 | 15 | 2 | | | 130 | 50 | 26 |
| 10 | 10 | 0.25 | 15 | 15 | 2 | | | 140 | 50 | 10 |
| 11 | 1 | 0.25 | 15 | 15 | 2 | | | 110 | 20 | 8.5 |
| 12 | 1 | 0.25 | 15 | 15 | 2 | | | 110 | 35 | 5 |
| 13 | 10 | 0.50 | 15 | 15 | 2 | | | 110 | 50 | 60 |
| 14 | 10 | 0.125 | 15 | 15 | 2 | | | 110 | 50 | 150 |
| 15 | 1 | 0.25 | 15 | 15 | .05 | | | 110 | 50 | 11 |
| 16 | 1 | 0.25 | 15 | 15 | 0.5 | | | 110 | 50 | 3.5 |
| 17 | 6.67 | 0.25 | 10 | 20 | 0.5 | | | 100 | 50 | ① |
| 18 | 6.67 | 0.25 | 20 | 10 | 0.5 | | | 110 | 50 | 30 |
| 19 | 10 | 0.25 | 5 | | | 25 | | 110 | 50 | 60 |
| 20 | 10 | 0.25 | 5 | | | | 25 | 110 | 50 | 100 |

*Solvents
NMP refers to N-methyl pyrrolidone.
MC refers to methyl cellosolve.
H$_2$O refers to water.
ETOH refers to ethanol.
HAL refers to acetic acid.
①— 90.8 percent sorbitol after 30 minutes.

EXAMPLE 21

1 gram of glucose,
15 ml of N-methyl pyrrolidone,
15 ml of methyl cellosolve,
2 ml of water,
0.65 grams of ruthenium trichloride trihydrate, and
0.069 grams of triphenyl phosphine.

The hydrogenation reaction was conducted as in Example 4. At the end of 150 minutes ½ of the glucose had been hydrogenated. At the end of 180 minutes a sample remained from the reaction mixture contained 57 percent by weight sorbitol.

EXAMPLES 22 – 25

Employing the procedure described in Example 21 wherein the molar ratio of Ru:Pφ$_3$ was equal to 1:1 the amounts of ruthenium trichloride (RuCl$_3$ · 3H$_2$O) and triphenyl phosphine (Pφ$_3$) included in the reaction mixture were varied. The amounts of these components, the molar ratio thereof, and the half life periods obtained are given in the following table.

| Example | Ruthenium trichloride (grams) | Triphenyl phosphine (grams) | Ratio Ru:PO$_3$ | $t_{1/2}$ (min.) |
|---|---|---|---|---|
| 22 | .065 | 00.138 | 1:2 | 5 |
| 23 | .065 | 0.203 | 1:3 | 5 |
| 24 | .065 | 0.288 | 1:4 | 12 |
| 25 | .065 | 0.610 | 1:9 | 8 |

EXAMPLE 26

Into a 200 ml pop bottle there were added:
10 grams of glucose,
10 ml of N-methyl pyrrolidone,
15 ml of methyl cellosolve,
2 ml of water, and
.09 grams of concentrated HCl.

To the resulting solution there was added a solution of:

0.25 grams of ruthenium chloride triphenyl phosphine prepared as described in Example 1, dissolved in
5 ml of N-methyl pyrrolidone.

The hydrogenation reaction was carried out as described in Example 4 at a temperature of 110°C. and a hydrogen pressure of 50 psi.

The half life period was equal to 15 minutes and, after 100 minutes, a sample contained no glucose and 96 percent by weight sorbitol.

EXAMPLE 27

Into a 200 ml pop bottle there were added:
10 grams of glucose,
10 ml of N-methyl pyrrolidone,
15 ml of methyl cellosolve,
2 ml of water, and
0.4 grams of toluene sulfonic acid.

To the resulting solution there was added a solution of:
0.25 grams of ruthenium dichloride triphenyl phosphine prepared as described in Example 1, dissolved in
5 ml of N-methyl pyrrolidone.

The hydrogenation reaction was carried out as described in Example 4 at a temperature of 110°C and a hydrogen pressure of 50 psi.

The half life period was equal to 15 minutes and, after 110 minutes, a sample contained no glucose and 95.2 percent by weight sorbitol.

EXAMPLES 28 – 34

Several substrates were hydrogenated by first dissolving the substrate in 10 ml of N-methyl pyrrolidone, 15 ml of methyl cellosolve and 2 ml of water and adding to the resulting solution a solution of 0.25 grams of ruthenium dichloride triphenyl phosphine prepared as described in Example 1, and 5 ml of N-methyl pyrrolidone. The hydrogenation was carried out as in Example 4 except that the temperature was 75°C. rather than 110°C. The substrate, amounts employed, and half life periods are given in the following table.

| Example | Substrate | Amount (grams) | $t_{1/2}$ (min.) |
|---|---|---|---|
| 28 | mannose | 2 | 20 |
| 29 | fructose | 2 | over 30 |
| 30 | arabinose | 2 | less than 10 |
| 31 | xylose | 2 | 13 |
| 32 | ribose | 2 | less than 10 |
| 33 | 1,3 dihydroxy acetone | 1 | 18 |
| 34 | 1,3 dichloro acetone | 1.4 | 10 |

EXAMPLE 35

Into a 200 ml pop bottle there were added:
3.33 grams of glucose,
10 ml of N-methyl pyrrolidone,
15 ml of methyl cellosolve,
2 ml of water, and
0.1 gram of concentrated hydrochloric acid.

To the resulting solution there was added a solution of 0.25 grams of ruthenium hydridochloride triphenyl phosphine prepared as described in Example 2, dissolved in 5 ml of N-methyl pyrrolidone.

The hydrogenation reaction was carried out as described in Example 4 at a temperature of 110°C. and a hydrogen pressure of 50 psi.

The half life period was equal to 16 minutes. In a similar experiment conducted without the addition of HCl the half life period was equal to 100 minutes.

EXAMPLE 36

Into a 200 ml pop bottle there were added:
10 grams of corn starch hydrolyzate,
11 ml of methyl cellosolve, and
6 ml of N-methyl pyrrolidone.

To the resulting solution there was added solution of 0.25 grams of ruthenium dichloro triphenyl phosphine, prepared as described in Example 1, dissolved in 5 ml of N-methyl pyrrolidone.

The hydrogenation reaction was carried out as described in Example 4 at a temperature of 110°C and a hydrogen pressure of 50 psi.

After 3 hours, 94 percent by weight of sorbitol was obtained.

EXAMPLE 37

Into a 17 ml pop bottle there were added:
0.8 grams of maltotriose,
3 ml of methyl cellosolve, and
0.3 ml of water.

To the resulting solution there was added a solution of 0.1 gram of dichloro (tris(triphenyl phosphine) ruthenium, prepared as described in Example 1, dissolved in 2 ml of N-methyl pyrrolidone.

The hydrogenation reaction was carried out as described in Example 4 at a temperature of 110°C and a hydrogen pressure of 50 psi.

After 3 hours, a thin layer chromatogram showed only maltotriitol.

EXAMPLE 38

Preparation of Ruthenium Dichloro Tris(Para-Methoxy Phenyl) Phosphine

Into a pop bottle there was added a solution of 60 milligrams of ruthenium trichloride trihydrate dissolved in 5 ml of N-methyl pyrrolidone and 0.25 grams of tris(para-methoxy phenyl) phosphine. After exposure to hydrogen for 15 hours the reaction mixture turned a dark red color.

Hydrogenation Reaction

Into a 200 ml pop bottle there were added 3.3 grams of glucose, 10 ml of N-methyl pyrrolidone, 15 ml of methyl cellosolve, and 3 ml of water. To the resulting solution there was added the solution of catalyst prepared as described above.

The hydrogenation reaction was carried out as described in Example 4 at a temperature of 110°C and a hydrogen pressure of 50 psi. The half life period was equal to 20 minutes.

What is claimed is:
1. A homogeneous hydrogenation process comprising contacting a solution of a substrate selected from the group consisting of monosaccharides, disaccharides, trisaccharides, polysaccharides and corn starch hydrolyzate with hydrogen under positive pressure in the presence of a catalyst comprising a ruthenium triphenyl phosphine complex having the following general formula:
    RuHCl(PR′$_3$)$_3$
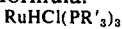
wherein R′ is phenyl, p-methyl phenyl, or p-methoxy phenyl and a strong acid having a pKa equal to less than about 1 and a prototropic organic solvent capable of dissolving the substrate and catalyst at room temperature or at the reaction temperature and about 1 percent to about 30 percent of water based on the total weight of the system.

2. A homogeneous hydrogenation process comprising contacting a solution of a substrate selected from the group consisting of monosaccharides, disaccharides, trisaccharides, polysaccharides and corn starch hydrolyzate with hydrogen in the presence of a catalyst comprising a ruthenium triphenyl phosphine complex having the following general formula:
    RuHCl(PR′$_3$)$_3$
wherein R′ is phenyl, p-methyl phenyl, or p-methoxy phenyl and a stron acid having a pKa value equal to less than about one wherein the amount of acid is equal to at least 1 mol per mol of the ruthenium triphenyl phosphine complex, the process is carried out under positive hydrogen pressure and in an inert prototropic solvent in an amount sufficient to dissolve the substrate and the catalyst and about 1 percent to about 30 percent of water based on the total weight of the system.

3. A process, as claimed in claim 1, wherein the ruthenium triphenyl phosphine complex and strong acid are prepared in situ.

4. A process, as claimed in claim 3, wherein the ruthenium triphenyl phosphine complex is prepared from $RuCl_2(Pr'_3)_3$ wherein R' is phenyl, p-methyl phenyl or p-methoxy phenyl.

5. A process, as claimed in claim 3, wherein the ruthenium triphenyl phosphine complex is prepared from $RuCl_3$ and $PR'_3$ wherein R' is phenyl, p-methyl phenyl or p-methoxy phenyl.

6. A process, as claimed in claim 1, wherein R' is phenyl.

7. A process, as claimed in claim 1, wherein the strong acid is hydrochloric acid.

8. A process, as claimed in claim 1, wherein the reaction is carried out in a mixed solvent system comprising
   a. an prototropic organic polar solvent,
   b. a weakly basic solvent having a pKb equal to less than about 13 in an amount equal to at least 1 mol of strong acid in the reaction system, and
   c. water.

9. A process, as claimed in claim 8, wherein the solvent system comprises
   a. methyl cellosolve,
   b. N-methyl pyrrolidone, and
   c. water.

10. A process, as claimed in claim 9, wherein the solvents are utilized in a volumetric ratio of a:b:c of 15:15:2.

11. A process, as claimed in claim 1, wherein the reaction is carried out at a temperature in the range of from about 75°C to about 150°C.

12. A process, as claimed in claim 1, wherein the reaction is carried out at a pressure of from about 20 psi to about 1500 psi.

13. A process, as claimed in claim 1, wherein the substrate is a monosaccharide.

14. A process, as claimed in claim 1, wherein the monosaccharide contains at least 4 carbon atoms.

15. A process, as claimed in claim 13, wherein the monosaccharide contains from 4 to 6 carbon atoms.

16. A process, as claimed in claim 13, wherein the monosaccharide is glucose.

17. A process, as claimed in claim 1, wherein the substrate is corn starch hydrolyzate.

\* \* \* \* \*